(12) United States Patent
Ikemoto et al.

(10) Patent No.: US 6,930,211 B2
(45) Date of Patent: Aug. 16, 2005

(54) PRODUCTION METHODS OF CITALOPRAM AND INTERMEDIATES THEREFOR

(75) Inventors: Tetsuya Ikemoto, Osaka (JP); Masami Igi, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/650,876

(22) Filed: Aug. 28, 2003

(65) Prior Publication Data

US 2004/0044232 A1 Mar. 4, 2004

Related U.S. Application Data

(60) Continuation of application No. 10/176,721, filed on Jun. 21, 2002, now abandoned, which is a division of application No. 09/997,992, filed on Nov. 30, 2001, now Pat. No. 6,433,195, which is a division of application No. 09/909,596, filed on Jul. 20, 2001, now Pat. No. 6,395,910, which is a division of application No. 09/648,048, filed on Aug. 25, 2000, now Pat. No. 6,310,222.

(30) Foreign Application Priority Data

Nov. 1, 1999 (JP) .......................................... 11-311703

(51) Int. Cl.$^7$ .............................................. C07C 37/55
(52) U.S. Cl. ................................................... 568/753
(58) Field of Search .......................... 549/300; 568/753

(56) References Cited

U.S. PATENT DOCUMENTS

| | | |
|---|---|---|
| 3,642,997 A | 2/1972 | Shen et al. |
| 3,835,167 A | 9/1974 | Pfister |
| 4,136,193 A | 1/1979 | Bøges&et al. |
| 4,898,864 A | 2/1990 | Maignan et al. |
| 5,061,810 A | 10/1991 | Ramachandran |
| 6,291,689 B1 | 9/2001 | Petersen et al. |
| 6,310,222 B1 | 10/2001 | Ikemoto et al. |
| 6,395,910 B2 | 5/2002 | Ikemoto et al. |
| 6,420,574 B2 | 7/2002 | Petersen et al. |
| 6,433,195 B1 | 8/2002 | Ikemoto et al. |
| 6,433,196 B1 | 8/2002 | Ikemoto et al. |
| 6,458,975 B1 | 10/2002 | Ikemoto et al. |
| 2001/0027256 A1 | 10/2001 | Petersen et al. |
| 2002/0004604 A1 | 1/2002 | Petersen et al. |
| 2002/0095051 A1 | 7/2002 | Ikemoto et al. |
| 2002/0151728 A1 | 10/2002 | Ikemoto et al. |
| 2003/0060640 A1 | 3/2003 | Petersen |
| 2003/0083508 A1 | 5/2003 | Petersen et al. |
| 2003/0109577 A1 | 6/2003 | Liljegren et al. |
| 2003/0114692 A1 | 6/2003 | Petersen et al. |
| 2003/0134895 A1 | 7/2003 | Petersen et al. |

FOREIGN PATENT DOCUMENTS

| | | |
|---|---|---|
| DE | 26 57 013 A1 | 7/1977 |
| EP | 0 178 184 A1 | 4/1986 |
| JP | 04-210687 | 7/1992 |
| WO | WO 93/14055 | 7/1993 |
| WO | WO 98/19511 | 5/1998 |
| WO | WO 99/30548 | 6/1999 |
| WO | WO 00/26167 | 5/2000 |
| WO | WO 01/68632 | 9/2001 |
| WO | WO 01/85712 | 11/2001 |

OTHER PUBLICATIONS

Allinger, "Organic Chemistry," pp. 452–455 (1971).

Beilstein, EIII/IV 18, Syst. Nr. 2619/H418 (1951).

Bigler et al., "Quantitative Structure–Activity Relationships in a Series of Selective 5–HT Uptake Inhibitors," *European Journal of Medicinal Chemistry, Editions Scientifique Elsevier*, 12 (3), 289–295 (XP–000944915) (1977).

Carruthers, W., "Some Modern Methods of Organic Synthesis," 3$^{rd}$ Edition, *Chemistry Department—University of Exeter*, Cambridge University Press, Cambridge, Great Britain, pp. 457–478 (1986).

Constantinides et al., "Reactions of Molecules with Two Equivalent Functional Groups. 2. Acetylation of the Isomers of Bis(Hydroxymethyl)benzene," *Journal of Physical Organic Chemistry*, 3 (12), 789–798 (1990).

Dokunikhin et al., "Anthraquinone Derivatives. III. Synthesis of Fluoro–substituted 2–Anthraquinone–Carboxylic Acid and 2–Aminoanthraquinone,"*Chemical Abstracts*, 60 (13), 537b (1964).

Goethals et al., "Basicity of Benzophenones and Polysubstituted 2–Methylbenzophenones. Role of Molecular Twisting and Electronic Interactions in the Transmission of Substituent Effects," *Chemical Abstracts Service*, Database Accession No. 83:178083 (1975).

Gómez et al., "DTBB–Catalysed Lithiation of Chlorinated Benzylic Chlorides, Alcohols, Thiols or Amines," *Tetrahedron*, 54 (9), 1853–1866 (1998).

Huntress et al., "4–Nitrophthalimide," Organic Synthesis II, p. 459 (1943).

Kirmse et al., "Carbenes and the O—H Bond: Hydroxyalkyl–Substituted Arylcarbenes," *J. Org. Chem.*, 55 (8), 2325–2332 (1990).

Levy et al., "4–Aminophthalide and Some Derivatives," Journal of Chemical Society, p. 867 (1931).

(Continued)

*Primary Examiner*—Taofiq Solola
(74) *Attorney, Agent, or Firm*—Leydig, Voit & Mayer, Ltd.

(57) ABSTRACT

The present invention provides a production method of a compound of the formula

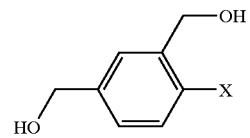

wherein X is chlorine atom, bromine atom or iodine atom, as well as a production method of citalopram and intermediates therefor.

6 Claims, No Drawings

OTHER PUBLICATIONS

"Phthalides Substituted at 5," Bull. Soc. Sci. Bretagne, Chapter II: 35–43 (1951).

Rigaudy et al., "Transformations Thermiques des Photoxydes *Meso* des Acenes–IV," *Tetrahedron,* The International Journal for the Rapid Publication of Critical Reviews and Original Research Communications in Organic Chemistry, Pergamon Press, Oxford, Great Britain, 34, 113–121 (1978).

Verbeerst et al., "Friedel–Crafts Acylation. V. Polar and Steric Substituent Effects in the Reaction of Disubstituted Benzoyl Chlorides Carrying a Constant Ortho–Substituent," *Chemical Abstracts Service,* Database Accession No. 70:2962 (1969).

PRODUCTION METHODS OF CITALOPRAM AND INTERMEDIATES THEREFOR

CROSS REFERENCE TO RELATED APPLICATIONS

This patent application is a continuation of U.S. patent application Ser. No. 10/176,721, filed Jun. 21, 2002, now abandoned, which is a divisional of U.S. patent application Ser. No. 09/997,992, filed Nov. 30, 2001, now U.S. Pat. No. 6,433,195, which is a divisional of U.S. patent application Ser. No. 09/909,596, filed Jul. 20, 2001, now U.S. Pat. No. 6,395,910, which is a divisional of U.S. patent application Ser. No. 09/648,048, filed Aug. 25, 2000, now U.S. Pat. No. 6,310,222.

TECHNICAL FIELD OF THE INVENTION

The present invention relates to a production method of a 5-phthalancarbonitrile compound useful as an intermediate for citalopram, which is an antidepressant, an intermediate for the 5-phthalancarbonitrile compound and a production method of the intermediate for the 5-phthalancarbonitrile compound. More particularly, the present invention relates to a production method of a 5-phthalancarbonitrile compound via a novel compound of the formula [I] to be mentioned later, based on a completely new viewpoint.

BACKGROUND OF THE INVENTION

The 5-phthalancarbonitrile compound of the formula [VI]

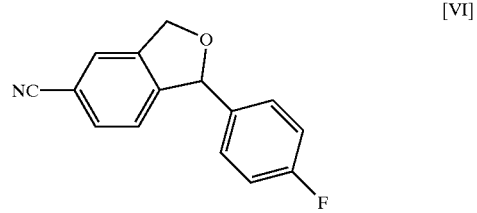

[VI]

(hereinafter to be also referred to as compound [VI]) is a compound useful as a synthetic intermediate for citalopram of the formula [VII]

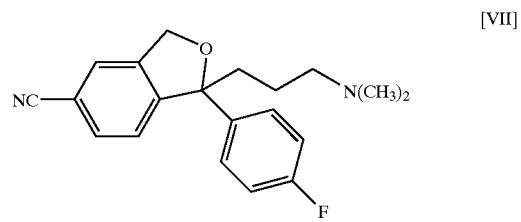

[VII]

which is an antidepressant. The production method of the 5-phthalancarbonitrile compound is known to be as shown in the following scheme (WO98/19511).

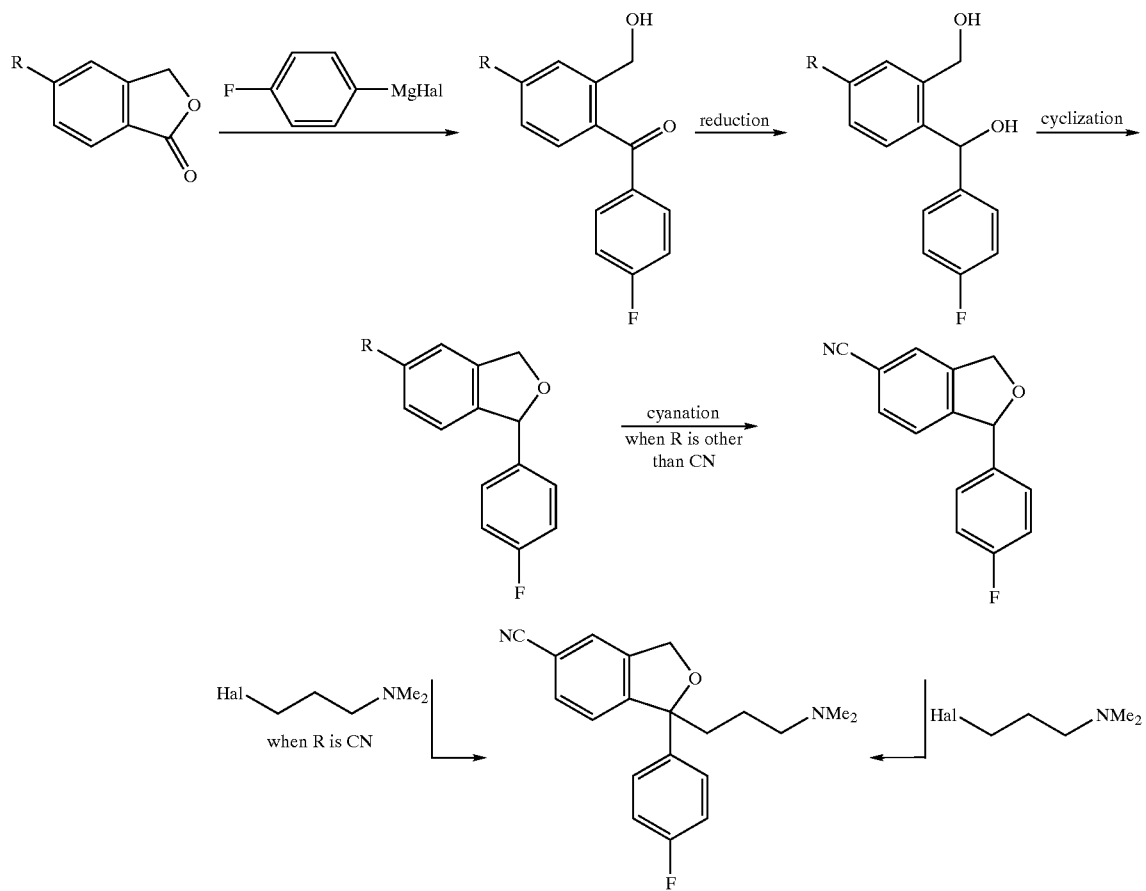

wherein R is cyano, alkyloxycarbonyl having 2 to 6 carbon atoms or alkylaminocarbonyl having 2 to 6 carbon atoms, and Hal is a halogen atom.

According to this method, when R is other than cyano, cyanation is necessary after reduction and ring closure reaction. For example, when R is alkyloxycarbonyl, cyanation is carried out by the three steps of hydrolysis, amidation and reaction with chlorosulfonyl isocyanate, and when R is alkylaminocarbonyl, cyanation is carried out by a reaction with thionyl chloride or phosphorus pentachloride. In these methods, reagents undesirable to the environment, such as chlorosulfonyl isocyanate, thionyl chloride and phosphorus pentachloride, are used, and when R is alkyloxycarbonyl, cyanation is carried out by 3 steps, which is not necessarily simple or easy.

When R is cyano, the production method of the starting material, 5-cyanophthalide, needs to be improved. To be specific, 5-cyanophthalide is known to be obtained by the reaction of a diazonium salt derived from 5-aminophthalide with potassium cyanide in the presence of copper sulfide (Bull. Soc. Sci. Bretagne, 26, 1951, 35). This method is not desirable in that a toxin and a heavy metal salt are involved, such as potassium cyanide and copper sulfide. In addition, synthesis of 5-aminophthalide requires a dangerous reaction of nitration of phthalimide (Organic Synthesis II, 459), and further, reduction to amino by tin chloride and semi-reduction of phthalimide by zinc (J. Chem. Soc., 1931, 867), generating a waste heavy metal that is industrially undesirable.

It is therefore an object of the present invention to provide a production method of a 5-phthalancarbonitrile compound, which places only a small burden on the environmental and which is safe.

SUMMARY OF THE INVENTION

Such object can be achieved by the present invention detailed in the following.

In accordance with the present invention, there are provided a method of producing a 5-phthalancarbonitrile compound (compound of the aforementioned formula [VI]) useful as an intermediate for citalopram, which is safe and imposes less environmental burden, the method comprising using a compound of the formula [A]

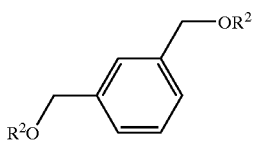

wherein $R^2$ is alkanoyl having 2 to 5 carbon atoms (hereinafter to be also referred to as compound [A]) as a starting material, and a novel compound of the formula [I]

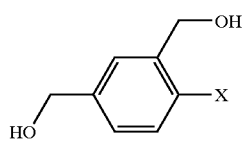

wherein X is chlorine atom, bromine atom or iodine atom (hereinafter to be also referred to as compound [I]) as a key intermediate, without using thionyl chloride and the like; novel compounds of the following formulas [II], [III], [IV] and [V], that can be used for the production method of the 5-phthalancarbonitrile compound of the present invention:

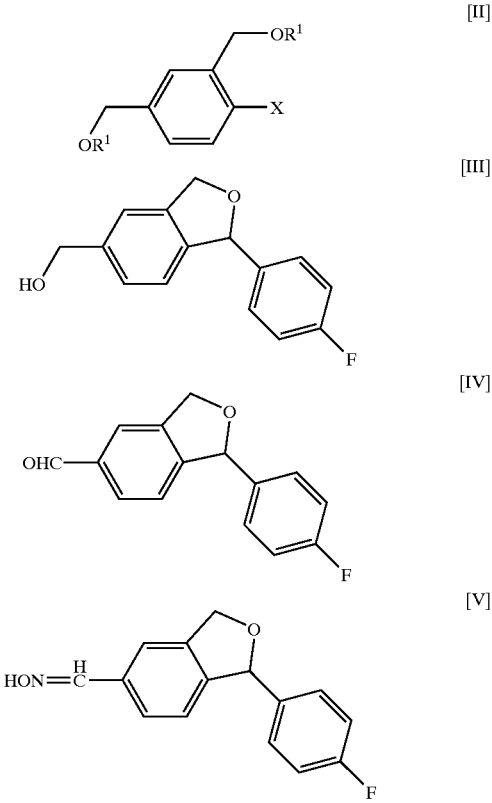

wherein $R^1$ is alkanoyl having 2 to 5 carbon atoms, alkyl having 1 to 5 carbon atoms, tetrahydropyran-2-yl, alkoxymethyl wherein the alkoxyl moiety has 1 to 5 carbon atoms, 1-alkoxyethyl wherein the alkoxyl moiety has 1 or 3 to 10 carbon atoms, or trialkylsilyl wherein each alkyl moiety has 1 to 5 carbon atoms, and X is chlorine atom, bromine atom or iodine atom (hereinafter to be also referred to as compound [II], compound [III], compound [IV] and compound [V], respectively); and the production methods thereof. Every conventional production method of citalopram goes through a 5-substituted phthalide compound (e.g., 5-formylphthalide), but the method of the present invention goes through the compound [I], employing a completely new synthetic strategy.

DETAILED DESCRIPTION OF THE INVENTION

The symbols used in the present specification are defined in the following.

With regard to alkyl, alkoxy and the like used in the present invention, they are linear unless a prefix (e.g., iso, neo etc.) or a symbol (e.g., sec-, tert- etc.) is attached. For example, a simple "propyl" means linear propyl.

The alkanoyl having 2 to 5 carbon atoms at $R^1$, $R^2$, $R^{1'}$ and $R^{1a}$ is linear or branched chain alkanoyl preferably having 2 to 5 carbon atoms, such as acetyl, butanoyl, propanoyl, isopropanoyl, pentanoyl, pivaloyl and the like, with preference given to acetyl, propanoyl and pivaloyl.

The alkyl having 1 to 5 carbon atoms at $R^1$, $R^{1'}$ and $R^{1b}$ is linear or branched chain alkyl preferably having 1 to 4 carbon atoms, such as methyl, ethyl, propyl, isopropyl, butyl, isobutyl, sec-butyl, tert-butyl, pentyl, isopentyl and the like, with preference given to methyl and tert-butyl.

The alkoxymethyl at $R^1$, $R^{1'}$ and $R^{1b}$, wherein the alkoxyl moiety has 1 to 5 carbon atoms, is alkoxymethyl having linear or branched chain alkoxy preferably having 1 or 2 carbon atoms, such as methoxymethyl, ethoxymethyl, propoxymethyl, isopropoxymethyl, butoxymethyl, isobutoxymethyl, sec-butoxymethyl, tert-butoxymethyl, pentoxymethyl, isopentoxymethyl and the like, with preference given to methoxymethyl and ethoxymethyl.

The 1-alkoxyethyl at $R^1$, wherein the alkoxyl moiety has 1 or 3 to 10 carbon atoms, is linear, branched chain or cyclic 1-alkoxyethyl wherein the alkoxyl moiety preferably has 1 or 3 to 6 carbon atoms, such as 1-methoxyethyl, 1-propoxyethyl, 1-isopropoxyethyl, 1-butoxyethyl, 1-isobutoxyethyl, 1-sec-butoxyethyl, 1-tert-butoxyethyl, 1-pentoxyethyl, 1-isopentoxyethyl-, 1-hexyloxyethyl, 1-cyclohexyloxyethyl, 1-heptyloxyethyl, 1-octyloxyethyl, 1-nonyloxyethyl, 1-decyloxyethyl and the like, with preference given to 1-propoxyethyl, 1-butoxyethyl and 1-cyclohexyloxyethyl.

The 1-alkoxyethyl at $R^{1'}$ and $R^{1b}$, wherein the alkoxyl moiety has 1 to 10 carbon atoms, is linear, branched chain or cyclic 1-alkoxyethyl wherein the alkoxyl moiety preferably has 1 to 6 carbon atoms, such as 1-methoxyethyl, 1-ethoxyethyl, 1-propoxyethyl, 1-isopropoxyethyl, 1-butoxyethyl, 1-isobutoxyethyl, 1-sec-butoxyethyl, 1-tert-butoxyethyl, 1-pentoxyethyl, 1-isopentoxyethyl, 1-hexyloxyethyl, 1-cyclohexyloxyethyl, 1-heptyloxyethyl, 1-octyloxyethyl, 1-nonyloxyethyl, 1-decyloxyethyl and the like, with preference given to 1-ethoxyethyl, 1-propoxyethyl, 1-butoxyethyl and 1-cyclohexyloxyethyl.

The alkyl of the trialkylsilyl at $R^1$, $R^{1'}$ and $R^{1b}$, wherein each alkyl moiety has 1 to 5 carbon atoms, is independently linear or branched chain alkyl preferably having 1 to 4 carbon atoms, such as methyl, ethyl, propyl, isopropyl, butyl, isobutyl, sec-butyl, tert-butyl, pentyl, isopentyl and the like, with preference given to methyl and tert-butyl. The trialkylsilyl may be, for example, trimethylsilyl, triethylsilyl, tripropylsilyl, triisopropylsilyl, tributylsilyl, triisobutylsilyl, trisecbutylsilyl, tripentylsilyl, triisopentylsilyl, tert-butyldimethylsilyl and the like, with preference given to trimethylsilyl, tributylsilyl and tert-butyldimethylsilyl.

The present invention is explained in detail in the following.

Production Method of Compound [I]

The novel compound [I] can be efficiently obtained by subjecting compound [A] to one of chlorination, bromination and iodination, and then to the elimination of the alkanoyl group. For example, chlorination, bromination or iodination, preferably bromination, is performed by reacting compound [A] with a halogenating agent in a reaction solvent to give a compound of the formula [II-a]

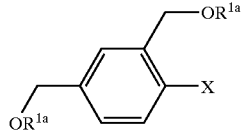
[II-a]

wherein X is chlorine atom, bromine atom or iodine atom and $R^{1a}$ is alkanoyl having 2 to 5 carbon atoms (hereinafter to be also referred to as compound [II-a]). This reaction is preferably carried out in the presence of a base. As used herein, X is preferably bromine atom in consideration of conversion of the compound of the formula [II-b] to a lithium compound or a Grignard reagent in the later step and $R^{1a}$ is particularly preferably acetyl in view of the easiness of synthesis and deprotection. The alkanoyl group is eliminated by adding the obtained compound [II-a] or a solution of compound [II-a] in an organic solvent, to an aqueous solution of an acid or base, preferably an acidic aqueous solution, to allow hydrolysis.

The starting compound [A] is preferably m-xylylene glycol diacetate, m-xylylene glycol dipropionate or m-xylylene glycol dipivalate.

The reaction solvent to be used for chlorination, bromination and iodination is, for example, glacial acetic acid, aqueous acetic acid solution (concentration: 60–100 wt %, preferably 80–100 wt %), water, monochlorobenzene, o-dichlorobenzene, ethyl acetate, tert-butyl methyl ether, and methanol, ethanol, isopropyl alcohol, acetone etc., that may contain water, with preference given to glacial acetic acid, aqueous acetic acid solution, methanol, o-dichlorobenzene and ethyl acetate. The reaction solvent is used in an amount of generally 1 L–20 L, preferably 3 L–10 L, per 1 kg of compound [A].

The base to be used for chlorination, bromination and iodination is sodium acetate, potassium acetate, sodium hydroxide, potassium hydroxide, sodium carbonate, potassium carbonate, sodium methoxide, sodium ethoxide and the like, preferably sodium acetate, potassium acetate, sodium hydroxide, potassium hydroxide, sodium carbonate and potassium carbonate. The base is used in an amount of generally 0.1 equivalent–10 equivalents, preferably 0.8 equivalent–6 equivalents, per the amount of compound [A].

The halogenating agent to be used for chlorination, bromination and iodination is bromine, chlorine, N-bromosuccinimide, N-chlorosuccinimide, sulfuryl chloride and the like, preferably bromine and N-bromosuccinimide. The halogenating agent is used in an amount of generally 0.8 mol–8 mol, preferably 2 mol–6 mol, per 1 mol of compound [A].

For chlorination and bromination, a catalyst may be added to accelerate the reaction. The catalyst may be a single metal such as iron, copper, zinc, aluminum and the like; or a metal halide such as iron(I) chloride, iron(II) chloride, aluminum chloride, aluminum bromide, copper(I) chloride, copper(II) chloride, magnesium chloride, magnesium bromide, magnesium iodide, titanium tetrachloride, zinc chloride, zinc bromide, zinc iodide and the like, with preference given to iron, iron(I) chloride, iron(II) chloride, magnesium chloride, magnesium bromide, zinc chloride, zinc bromide and zinc iodide. The catalyst is used in an amount of generally 0.0001 mol–0.5 mol, preferably 0.001 mol–0.2 mol, per 1 mol of compound [A].

The reaction temperature of chlorination, bromination and iodination is generally from −30° C. to 80° C., preferably from 0° C. to 50° C., and the reaction time is generally 30 min–24 hr, preferably 2 hr–18 hr.

When compound [A] is subjected to chlorination, bromination or iodination, a 2,6-disubstituted compound may be produced as a halide, besides the compound [II-a] which is a 2,4-disubstituted compound. Such halide is isolated by, for example, pouring the reaction mixture to a reducing aqueous solution (e.g., aqueous sodium sulfite solution and aqueous sodium thiosulfate solution etc.) under ice-cooling, or pouring a reducing aqueous solution into the reaction mixture, adding an organic solvent; extraction and evaporation of the solvent. The compound [II-a] can be isolated from the mixture of halide by silica gel column chromatography, recrystallization and the like. The compound [II-a] may or may not be isolated from the mixture of halide. When the compounds are subjected to the next step without isolation, the corresponding 2,6-disubstituted compound, such as 2,6-disubstituted compound of compound [I] and 2,6-disubstituted compound of the compound of the formula [II-b] to be mentioned later, is obtained in each step together with the reaction product.

The amount of water to be used for elimination of the alkanoyl group is generally 0.5 L–20 L, preferably 3 L–10 L, per 1 kg of halide (mixture when halide is a mixture). A solvent inert to the reaction may be concurrently used, such as alcohol solvent (e.g., methanol, ethanol etc.), tetrahydrofuran (THF), dioxane and the like, which may be used to dissolve halide. When the solvent is used for dissolution of halide, it is used in an amount of generally 0.5 L–20 L, preferably 2 L–10 L, per 1 kg of halide (mixture when halide is a mixture).

The acid to be used for the elimination of the alkanoyl group is not particularly limited as long as it is typically used for this purpose. Examples thereof include inorganic acid such as hydrochloric acid, hydrobromic acid, hydrofluoric acid, sulfuric acid, phosphoric acid and the like; organic acid such as formic acid, acetic acid, propionic acid, trifluoroacetic acid, methanesulfonic acid, trifluoromethanesulfonic acid and the like; and the like, with preference given to hydrochloric acid, hydrobromic acid and sulfuric acid. The amount of the acid to be used is generally 0.001 kg–10 kg, preferably 0.01 kg–0.3 kg, per 1 kg of halide (mixture when halide is a mixture).

The base to be used for the elimination of the alkanoyl group is not particularly limited as long as it is typically used for this purpose. Examples thereof include inorganic base such as hydroxide, carbonate or hydrogencarbonate of alkali metal (e.g., lithium, sodium, potassium etc.) or alkaline earth metal (e.g., calcium, magnesium etc.) and alkoxide (e.g., methoxide, ethoxide etc.) of alkali metal, and organic base such as trialkylamine (e.g., trimethylamine, triethylamine etc.), with preference given to sodium hydroxide, potassium hydroxide, potassium carbonate and sodium methoxide. The amount of the base to be used is generally 0.8 equivalent–10 equivalents, preferably 1 equivalent–5 equivalents, per halide (mixture when halide is a mixture).

The reaction temperature of the elimination of the alkanoyl group is generally from –20° C. to 100° C., preferably from 10° C. to 80° C., and the reaction time is generally 10 min–24 hr, preferably 30 min–8 hr.

The compound [I] is isolated by a conventional method, such as crystallization after neutralization of the reaction mixture.

Production Method of Compound [II']

A compound of the formula [II']

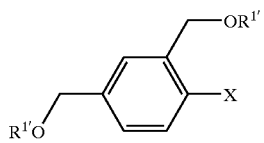

[II']

wherein $R^{1'}$ is alkanoyl having 2 to 5 carbon atoms, alkyl having 1 to 5 carbon atoms, tetrahydropyran-2-yl, alkoxymethyl wherein the alkoxyl moiety has 1 to 5 carbon atoms, 1-alkoxyethyl wherein the alkoxyl moiety has 1 to 10 carbon atoms, or trialkylsilyl wherein each alkyl moiety has 1 to 5 carbon atoms, and X is chlorine atom, bromine atom or iodine atom (hereinafter to be referred to as compound [II']), consists of compound [II-a] and a compound of the formula [II-b]

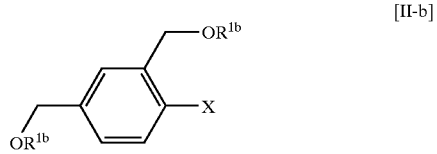

[II-b]

wherein $R^{1b}$ is alkyl having 1 to 5 carbon atoms, tetrahydropyran-2-yl, alkoxymethyl wherein the alkoxyl moiety has 1 to 5 carbon atoms, 1-alkoxyethyl wherein the alkoxyl moiety has 1 to 10 carbon atoms or trialkylsilyl wherein each alkyl moiety has 1 to 5 carbon atoms, and X is chlorine atom, bromine atom or iodine atom (hereinafter to be referred to as compound [II-b]). A compound wherein only 1-ethoxyethyl is excluded from the substituents at $R^1$ of compound [II'] corresponds to novel compound [II]. The compound [II'] can be obtained by (a) converting the hydroxyl group of compound [I] to alkoxy having 1 to 5 carbon atoms, tetrahydropyran-2-yloxy, alkoxymethoxy wherein the alkoxyl moiety has 1 to 5 carbon atoms, 1-alkoxyethbxy wherein the alkoxyl moiety has 1 to 10 carbon atoms or trialkylsilyloxy wherein each alkyl moiety has 1 to 5 carbon atoms, or by (b) subjecting compound [A] to chlorination, bromination or iodination.

The step (a) is explained in the following. By (a), compound [II-b] can be obtained. The hydroxyl group can be converted to each group by any method generally used for converting hydroxyl group to such group. It is converted to 1-alkoxyethoxy by, for example, reacting compound [I] with alkyl vinyl ether of the formula: $R^3CH=CH_2$ wherein $R^3$ is alkoxy having 1 to 10 carbon atoms, in a reaction solvent in the presence of a catalyst.

The starting compound [I] is preferably 2,4-bis (hydroxymethyl)bromobenzene in consideration of conversion to a lithium compound or a Grignard reagent of the compound [III] in the later step.

The alkoxy having 1 to 10 carbon atoms at $R^3$ of the above formula corresponds to alkoxy of 1-alkoxyethyl at the substituent $R^{1'}$ in compound [II'], wherein the alkoxyl moiety has 1 to 10 carbon atoms. The alkyl vinyl ether to be used for the reaction is, for example, methyl vinyl ether, ethyl vinyl ether, propyl vinyl ether, isopropyl vinyl ether, butyl vinyl ether, pentyl vinyl ether, cyclohexyl vinyl ether, hexyl vinyl ether, heptyl vinyl ether, octyl vinyl ether, nonyl vinyl ether, decyl vinyl ether and the like, preferably ethyl vinyl ether, propyl vinyl ether, butyl vinyl ether or cyclohexyl vinyl ether. The amount of the alkyl vinyl ether to be used is generally 2 mol–4 mol, preferably 2 mol–3 mol, per 1 mol of compound [I].

As the catalyst, for example, p-toluenesulfonic acid, methanesulfonic acid, sulfuric acid, hydrochloric acid, trifluoroacetic acid, trifluoromethanesulfonic acid, and an acidic ion exchange resin such as Amberlyst 15E, Amberlite IR-118 etc. are used, with preference given to p-toluenesulfonic acid, methanesulfonic acid, sulfuric acid and hydrochloric acid. These catalysts can be also used in the form of a hydrate. The amount of the catalyst to be used is generally 0.0001 mol–0.2 mol, preferably 0.0005 mol–0.01 mol, per 1 mol of compound [I].

The reaction solvent may be, for example, toluene, xylene, monochlorobenzene, methylene chloride, acetone, methyl ethyl ketone, methyl isobutyl ketone, ethyl acetate and the like, with preference given to toluene, xylene, monochlorobenzene and methylene chloride. The amount of the reaction solvent to be used is generally 1 L–20 L, preferably 2 L–12 L, per 1 kg of compound [I].

The reaction temperature is generally from -20° C. to 120° C., preferably from 0° C. to 60° C., and the reaction time is generally 10 min–10 hr, preferably 30 min–6 hr. The objective compound can be isolated by a conventional method (e.g., extraction, etc.).

Conversion to a group other than 1-alkoxyethoxy is performed according to a conventional method. For the conversion to alkoxy, for example, a reagent such as $R^4OH$ wherein $R^4$ is alkyl having 1 to 5 carbon atoms, $R^4Br$ wherein $R^4$ is as defined above, $R^4I$ wherein $R^4$ is as defined above, and $(R^4)_2SO_4$ wherein $R^4$ is as defined above is used; for the conversion to tetrahydropyran-2-yloxy, for example, a reagent such as 3,4-dihydro-2[H]-pyran is used; for the conversion to alkoxymethoxy, for example, a reagent, such as $R^5OCH_2OH$ wherein $R^5$ is alkyl having 1 to 5 carbon atoms, $R^5OCH_2OR^5$ wherein $R^5$ is as defined above, $R^5OCH_2Cl$ wherein $R^5$ is as defined above and $R^5OCH_2Br$ wherein $R^5$ is as defined above is used; and for the conversion to trialkylsilyloxy, for example, a reagent, such as $(R^6)_3SiCl$ wherein R is alkyl having 1 to 5 carbon atoms, is used. The definition of the above $R^4$–$R^6$ is the same as in the corresponding $R^{1'}$.

Then, compound [II-a] can be obtained by (b). The chlorination, bromination and iodination of compound [A] in (b) are carried out in the same manner as in those for the production of compound [I]. Bromination is preferably carried out in consideration of conversion of the compound [II-b] to a lithium compound or a Grignard reagent in the later step.

The compound [II-b] can be also obtained by a method other than the above-mentioned (a). For example, a compound [II-b] wherein $R^{1b}$ is alkyl having 1 to 5 carbon atoms can be obtained by Step 1: m-xylylene dichloride is reacted with an alkali metal alkoxide of the formula R'OM, wherein R' is alkyl having 1 to 5 carbon atoms and M is alkali metal, in a reaction solvent to give 1,3-bis(alkoxymethyl)benzene, and Step 2: the resulting compound is subjected to chlorination, bromination or iodination.

Step 1 is explained in detail in the following. In this step, alkali metal alkoxide is added to m-xylylene dichloride in a reaction solvent to give 1,3-bis(alkoxymethyl)benzene.

The reaction solvent in Step 1 is exemplified by alcohol solvent (e.g., methanol, ethanol, isopropyl alcohol, tert-butyl alcohol etc.), tetrahydrofuran (THF), tert-butyl methyl ether, toluene, monochlorobenzene, N,N-dimethylformamide, dimethyl sulfoxide and the like. The amount of the solvent to be used is generally 1 L–30 L, preferably 2 L–15 L, per 1 kg of m-xylylene dichloride.

The alkyl moiety of the alkali metal alkoxide in Step 1 is the same as those exemplified for the alkyl at $R^{1b}$ and examples of alkali metal include sodium, potassium and the like. Preferable examples of alkali metal alkoxide include sodium methoxide and potassium tert-butoxide. The amount of the alkali metal alkoxide to be used is generally 1.8 mol–4 mol, preferably 2 mol–3.2 mol, per 1 mol of m-xylylene dichloride.

The reaction temperature in Step 1 is generally from -30° C. to 100° C., preferably 20° C.–70° C., and the reaction time is generally 0.5 hr–10 hr, preferably 1 hr–6 hr.

The isolation of 1,3-bis(alkoxymethyl)benzene can be carried out by a conventional method, such as extraction and drying after evaporation of the solvent.

Step 2 can be carried out in the same manner as in chlorination, bromination, iodination in the production method of compound [I] and under the same reaction conditions. The reaction solvent, base, halogenating agent and catalyst to be used for the chlorination, bromination and iodination are the same as those exemplified for the production method of compound [I], wherein they are used in the same amounts as in the production method of compound [I]. The reaction product can be isolated in the same manner as in the production method of compound [I].

Production Method of Compound [III]

A novel compound [III] can be obtained by
(a) converting compound [II-b] to Grignard reagent or lithium compound,
(b) coupling the resulting compound with p-fluorobenzaldehyde and
(c) subjecting the obtained coupling compound to deprotection of $R^{1b}$ and cyclization.

The compound [II-b] is compound [I], wherein hydroxyl group has been protected, which is, after conversion to a lithium compound or a Grignard reagent, reacted with p-fluorobenzaldehyde. Therefore, X in the compound [II-b] is free of any particular limitation as long as compound [II-b] can be converted to a lithium compound or a Grignard reagent. Preferred is bromine atom in view of the quick conversion and the stability of the lithium compound or Grignard reagent after conversion. For easy deprotection, tetrahydropyran-2-yl, alkoxymethyl, where alkoxy has 1 to 5 carbon atoms, 1-alkoxyethyl, where alkoxy has 1 to 10 carbon atoms, and trialkylsilyl, where each alkyl has 1 to 5 carbon atoms, are preferable as $R^{1b}$, with more preference given to tetrahydropyran-2-yl, methoxymethyl and 1-alkoxyethyl, where alkoxy has 1 to 10 carbon atoms, particularly preferably 1-ethoxyethyl, 1-propoxyethyl, 1-butoxyethyl and 1-cyclohexyloxyethyl. From the easiness of synthesis, methyl and tert-butyl are particularly preferable.

As compound [II-b], preferred are 2,4-bis(1'-ethoxyethoxymethyl)bromobenzene, 2,4-bis(1'-butoxyethoxymethyl)-bromobenzene and 2,4-bis(1'-cyclohexyloxyethoxymethyl)bromobenzene.

The above-mentioned (a) to (c) are explained in this order in the following.

(a): The compound [II-b] can be converted to a Grignard reagent or a lithium compound by a method conventionally known, which is used for obtaining a Grignard reagent or a lithium compound from halide. For example, compound [II-b] is reacted with metal magnesium in an organic solvent, or a solution of an organic lithium compound in an organic solvent, and may be added dropwise to compound [II-b]. The metal magnesium or organic lithium compound is added in an amount generally necessary for converting a halide to a Grignard reagent or a lithium compound. For example, metal magnesium is added in an amount of generally 0.9 mol–3 mol, preferably 1 mol–1.5 mol, and the organic lithium compound is added in an amount of generally 0.9 mol–1.5 mol, preferably 1 mol–1.3 mol, both per 1 mol of compound [II-b]. Examples of the organic lithium compound include n-butyl lithium, phenyl lithium, methyl lithium, sec-butyl lithium and tert-butyl lithium, preferably n-butyl lithium and methyl lithium. For the easiness of the operation and the yield of the reaction, compound [II-b] is preferably converted to a lithium compound.

The organic solvent is exemplified by ether solvents (e.g., tetrahydrofuran (THF), tert-butyl methyl ether, dimethoxyethane, dibutyl ether, ethyl ether etc.), hexane, heptane, toluene, xylene and the like, with preference given to hexane, THF, tert-butyl methyl ether and dimethoxyethane. The amount of the organic solvent to be used is generally 1 L–30 L, preferably 5 L–20 L, per 1 kg of compound [II-b].

The reaction temperature in (a) is generally from −78° C. to 30° C., preferably from −50° C. to −10° C., and the reaction time is generally 10 min–6 hr, preferably 10 min–2 hr. The reaction mixture obtained in (a) can be isolated or purified by a conventional method. Alternatively, it may be subjected to the next reaction as it is obtained.

(b): p-Fluorobenzaldehyde is added dropwise to the reaction mixture of (a) for coupling reaction. The amount of p-fluorobenzaldehyde to be used is generally 0.8 mol–3 mol, preferably 1 mol–1.5 mol, per 1 mol of compound [II-b]. p-Fluorobenzaldehyde can be added as a solution in an organic solvent, wherein the organic solvent is free of any particular limitation and exemplified by tetrahydrofuran, tert-butyl methyl ether, dimethoxyethane, hexane, heptane and the like.

The reaction temperature in (b) is generally from −78° C. to 60° C., preferably from −50° C. to 30° C., and the reaction time is generally 10 min–6 hr, preferably 10 min–2 hr.

After the completion of the reaction, a basic aqueous solution (e.g., aqueous ammonium chloride solution), an acidic aqueous solution (e.g., aqueous acetic acid solution) and the like are added to hydrolyze the reaction product. The coupling compound after hydrolysis can be isolated by, for example, partitioning and evaporation of the solvent.

(c): The isolated coupling compound is reacted with an acid catalyst in a reaction solvent for the deprotection of $R^{1b}$ and cyclization. The method of addition is not particularly limited. For example, an acid catalyst may be added to the reaction mixture of the coupling compound. The reaction is preferably carried out under pressure of generally 2 kPa–110 kPa, preferably 5 kPa–80 kPa, while removing deprotected aldehydes having a low boiling point, thereby suppressing the occurrence of by-product.

The reaction solvent may be water alone, because the reaction proceeds sufficiently. A suitable organic solvent may be further added. The organic solvent to be added may be miscible with water or non-miscible with water. Examples thereof include methanol, ethanol, isopropyl alcohol, acetone, tetrahydrofuran, toluene and xylene. The amount of the reaction solvent to be used is generally 0.5 L–20 L, preferably 1 L–10 L, per 1 kg of compound [II-b].

The acid catalyst may be a typical mineral acid, acidic ion exchange resin and Lewis acid, preferably phosphoric acid, sulfuric acid, hydrochloric acid, p-toluenesulfonic acid, methanesulfonic acid, trifluoroacetic acid and trifluoromethanesulfonic acid. The amount of the acid catalyst to be used is generally 0.1 mmol–30 mol, preferably 0.1 mol–20 mol, per 1 mol of compound [II-b]. The acidic catalyst can be also used in the form of an aqueous solution.

The reaction temperature in (c) is generally 30° C.–150° C., preferably 50° C.–100° C., and the reaction time is generally 10 min–20 hr, preferably 1 hr–6 hr.

The objective compound (compound [III]) can be isolated by a conventional method (e.g., filtration, recrystallization etc.).

The compound [III] can be obtained via a Grignard reagent or lithium compound of compound [II-b] and then through a coupling compound of the formula

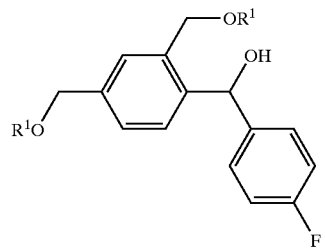

wherein $R^1$ is as defined above.

Production Method of Compound [IV]

The novel compound [IV] can be obtained by oxidation of compound [III]. The compound [III] has, as an easily oxidizable moiety, the 1-position and 3-position carbons, besides hydroxymethyl at the 5-position of the 1,3-dihydroisobenzofuran ring. Therefore, oxidation of compound [III] may accompany oxidation of the 1-position and 3-position carbons as a side reaction. However, when compound [III] is oxidized with hypochlorite in the presence of an N-oxy radical catalyst, hydroxymethyl is selectively oxidized to give compound [IV] at a high yield. To be specific, hypochlorite is added, preferably added dropwise as an aqueous solution, to a solution of compound [III] in an organic solvent in the presence of a base, a catalyst and an N-oxy radical catalyst, to give compound [IV].

The hypochlorite to be used for the oxidation may be, for example, sodium hypochlorite, potassium hypochlorite, calcium hypochlorite and the like, preferably sodium hypochlorite. The amount of the hypochlorite to be used is generally 0.8 mol–2 mol, preferably 0.85 mol–1.3 mol, per 1 mol of compound [III]. Sodium hypochlorite is preferably used in the form of an aqueous solution, where the concentration of the aqueous solution is generally 8 wt %–15 wt %, preferably 11 wt %–14 wt %.

The N-oxy radical catalyst to be used for the oxidation may be, for example, 4-substituted-2,2,6,6-tetramethyl-1-piperidinoxy. The amount of the catalyst to be used is generally 0.0001 mol–0.1 mol, preferably 0.0001 mol–0.01 mol, per 1 mol of compound [III]. Examples of the 4-position substituent include hydrogen atom, hydroxyl group, alkoxy having 1 to 10 carbon atoms, acyloxy having an aliphatic hydrocarbon residue having 1 to 10 carbon atoms, carbonylamino having an aliphatic hydrocarbon residue having 1 to 10 carbon atoms and the like, particularly preferably hydroxyl group from the viewpoint of the yield.

The alkoxy having 1 to 10 carbon atoms is preferably linear or branched chain alkoxy having 1 to 5 carbon atoms, such as methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy and decyloxy, preferably methoxy, ethoxy and isopropoxy.

The acyloxy having an aliphatic hydrocarbon residue having 1 to 10 carbon atoms is linear or branched chain acyloxy having an aliphatic hydrocarbon residue preferably having 1 to 6 carbon atoms, such as acetyloxy, propionyloxy, butyryloxy, isobutyryloxy, valeryloxy, isovaleryloxy, pivaloyloxy, hexanoyloxy, heptanoyloxy, octanoyloxy, nonanoyloxy, decanoyloxy, undecanoyloxy, acryloyloxy and methacryloyloxy, preferably acetyloxy and methacryloyloxy.

The carbonylamino having an aliphatic hydrocarbon residue having 1 to 10 carbon atoms is a linear or branched chain carbonylamino that has aliphatic hydrocarbon residue preferably having 1 to 6 carbon atoms, such as acetylamino, propionylamino, butyrylamino, isobutyrylamino, valerylamino, isovalerylamino, pivaloylamino, hexanoylamino, heptanoylamino, octanoylamino, nonanoylamino, decanoylamino, undecanoylamino, acryloylamino and methacryloylamino, preferably acetylamino.

Examples of 4-substituted-2,2,6,6-tetramethyl-1-piperidinoxy preferably include 4-hydroxy-2,2,6,6-tetramethyl-1-piperidinoxy, 4-methacryloyloxy-2,2,6,6-tetramethyl-1-piperidinoxy, 4-acetyloxy-2,2,6,6-tetramethyl-1-piperidnoxy and 4-acetylamino-2,2,6,6-tetramethyl-1-piperidinoxy, particularly preferably 4-hydroxy-2,2,6,6-tetramethyl-1-piperidinoxy from the aspect of yield.

The base is free of any particular limitation as long as it does not interfere with the reaction, and is exemplified by sodium hydrogencarbonate, sodium carbonate, potassium hydrogencarbonate, potassium carbonate, lithium carbonate and the like, with preference given to sodium hydrogencarbonate and potassium hydrogencarbonate. The amount of the base to be used is generally 0.01 mol–2 mol, preferably 0.1 mol–0.9 mol, per 1 mol of compound [III].

Examples of the catalyst include phase transfer catalyst such as tetrabutylammonium bromide, tetrabutylammonium chloride, tetrabutylammonium iodide, tetrabutylammonium sulfate, benzyltriethylammonium chloride, benzyltrimethylammonium chloride and the like, and metal halide catalyst such as potassium iodide, potassium bromide, sodium iodide, sodium bromide and the like, with preference given to tetrabutylammonium bromide, benzyltriethylammonium chloride, potassium iodide and potassium bromide. The amount of the catalyst to be used is generally 0.0001 mol–0.3 mol, preferably 0.01 mol–0.2 mol, per 1 mol of compound [III].

The organic solvent is not particularly limited and may be, for example, ethyl acetate, butyl acetate, acetone, ethyl methyl ketone, isobutyl methyl ketone, toluene, xylene, tert-butyl methyl ether and the like, with preference given to ethyl acetate, acetone, ethyl methyl ketone, isobutyl methyl ketone and toluene. The amount of the solvent to be used is generally 1 L–20 L, preferably 3 L–10 L, per 1 kg of compound [III].

The reaction temperature is generally from −30° C. to 100° C., preferably 0° C.–50° C., and the reaction time is generally 10 min–10 hr, preferably 10 min–2 hr.

The objective compound can be isolated by a conventional method such as extraction and crystallization.

Production Method of 5-phthalancarbonitrile Compound

The compound [VI] (5-phthalancarbonitrile compound) is an intermediate for the production of citalopram. It can be obtained by reacting a novel compound [IV] with hydroxylamine or a mineral acid salt thereof and via a novel compound [V] (compound [V] in the present invention includes both syn-compound and anti-compound), namely, through oximation (condensation) and dehydration reaction. It is preferable to (a) directly subject the compound [V] to dehydration reaction without isolation to make the manipulation simpler. For example, compound [IV] and hydroxylamine or a mineral acid salt thereof are added to an organic solvent and the mixture is heated as it is to give compound [VI].

For a higher purity of the compound [VI], (b) compound [V] is preferably isolated and then subjected to dehydration reaction. The compound [V] is obtained by reacting compound [IV] with hydroxylamine or a mineral acid salt thereof. By dehydrating compound [V], compound [VI] is obtained. To be specific, compound [IV] and hydroxylamine or a mineral acid salt thereof are added to an organic solvent, and the mixture is stirred to give compound [V]. The obtained compound [V] is isolated and heated to give compound [VI]. The compound [V] is isolated by a conventional method.

Examples of mineral acid salt of hydroxylamine include salts of hydroxylamine with hydrochloric acid, sulfuric acid, phosphoric acid, nitric acid and the like, with preference given to hydroxylamine hydrochloride and hydroxylamine sulfate.

The amount of the hydroxylamine or a mineral acid salt thereof to be used is generally 0.8 equivalent–5 equivalents, preferably 0.9 equivalent–2 equivalents, per compound [IV]. The hydroxylamine and a mineral acid salt thereof are used as they are or preferably in a solution state (e.g., methanol, ethanol, isopropyl alcohol, water, etc.). Depending on the scale of the reaction, it is particularly preferably added dropwise as a solution of hydroxylamine or a mineral acid salt thereof in methanol at 20–50° C.

Particularly when a hydroxylamine mineral acid salt is used, a suitable base is preferably added in an amount of 1 equivalent to 5 equivalents per hydroxylamine mineral acid salt. The base is free of any particular limitation as long as it exerts less influence on cyano, and examples thereof include organic base (e.g., triethylamine, tributylamine, dimethylaniline, pyridine, sodium methoxide, sodium ethoxide, potassium t-butoxide, sodium t-butoxide etc.), inorganic base (e.g., sodium carbonate, sodium hydrogencarbonate, sodium hydroxide, potassium carbonate, potassium hydrogencarbonate, potassium hydroxide etc.), with preference given to triethylamine. It is industrially preferable to add a base before the addition of a hydroxylamine mineral acid salt.

To carry out the dehydration reaction of compound [V] under mild conditions, a dehydrating agent may be further added. Examples of the dehydrating agent include acid anhydride (e.g., acetic anhydride, phthalic anhydride etc.), methanesulfonyl chloride, p-toluenesulfonyl chloride and the like, with preference given to the use of acetic anhydride from the aspects of the environment and yield. The amount of the dehydrating agent to be used is preferably 0.8 equivalent–5 equivalents, per hydroxylamine or a mineral acid salt thereof in the case of above (a), and 1 equivalent–10 equivalents, preferably 1 equivalent–5 equivalents, per compound [V] in the case of above (b). In the above (a), the dehydrating agent may be added simultaneously with hydroxylamine or a mineral acid salt thereof. However, the addition after the addition of hydroxylamine or a mineral acid salt thereof is preferable.

The organic solvent is free of any particular limitation as long as it does not interfere with the reaction, and examples thereof include methanol, ethanol, isopropyl alcohol, ethyl acetate, acetonitrile, toluene, xylene, chlorobenzene, 1,2-dichlorobenzene, N-methylpyrrolidone, nitroethane, dimethylformamide, dimethylacetamide, dimethyl sulfoxide, dichloromethane, and mixed solvents of the above, with preference given to acetonitrile, toluene, xylene, N-methylpyrrolidone, nitroethane, ethyl acetate, a mixed solvent of ethyl acetate and methanol, a mixed solvent of ethyl acetate and ethanol, a mixed solvent of ethyl acetate and isopropyl alcohol, and a mixed solvent of toluene and methanol. The amount of the organic solvent to be used is generally 0.5 L–50 L, preferably 1 L–20 L, per 1 kg of compound [IV] in the case of above (a), and generally 0.5 L–50 L, preferably 1 L–20 L, per 1 kg of compound [IV] in the case of above (b).

The reaction temperature in the above (a) is generally 50° C.–220° C., preferably 80° C.–150° C., and the reaction time is generally 1 hr–20 hr, preferably 2 hr–8 hr.

In the above (b), oximation (condensation) is conducted generally at 20–120° C., preferably 40–100° C., generally for 10 min–4 hr, preferably 30 min–2 hr, and dehydration reaction is carried out generally at 60–160° C., preferably 120–150° C., more preferably 125–150° C., generally for 30 min–8 hr, preferably 90 min–6 hr.

The objective compound is isolated by a conventional method such as extraction and crystallization after neutralization of the reaction mixture.

The starting compound [A] can be produced according to the method described in, for example, J. Phys. Org. Chem., 3(12), 789–98 (1990).

According to the method of the present invention, a 5-phthalancarbonitrile compound can be produced without using a reagent that imposes a great burden on the environment, such as heavy metal, metal cyanide and thionyl chloride. Moreover, the reaction proceeds efficiently throughout the entire steps.

The 5-phthalancarbonitrile compound can be converted to citalopram according to the method described in WO98/19511, thereby producing citalopram useful as an antidepressant.

The present invention is explained in detail by referring to illustrative examples, but the present invention is not limited by these examples in any way. In the examples, the unit % relative to the reagent is wt %.

EXAMPLE 1

Synthesis of 2,4-bis(acetoxymethyl)bromobenzene

To a suspension of m-xylylene glycol diacetate (28.4 g) and sodium acetate (55.2 g) dispersed in glacial acetic acid (130 ml) was added dropwise bromine (102.5 g) over 30 min at 15–20° C., and the mixture was stirred at 20–30° C. for 13 hr. The reaction mixture was poured into 10% aqueous sodium sulfite solution (700 ml) in an ice bath. The mixture was stirred and extracted twice with ethyl acetate (250 ml). The ethyl acetate layer was washed 3 times with 10% aqueous sodium hydrogencarbonate solution (300 ml) and the solvent was evaporated to give an about 93:7 mixture (37.6 g, 97.6%) of 2,4-bis(acetoxymethyl)bromobenzene and 2,6-bis(acetoxymethyl)bromobenzene as a yellow oil. 2,4-bis(Acetoxymethyl)bromobenzene was isolated by preparative HPLC and used in the measurement.
the mixture:
$n_D^{24}$ 1.5310;
IR(neat)ν=2957 (w), 1743 (s), 1476 (m), 1378 (m), 1226 (s), 1028 (s), 858 (w), 820 (w)cm$^{-1}$
2,4-bis(Acetoxymethyl)bromobenzene:
$^1$H-NMR(CDCl$_3$, 400 MHz)δ=2.11 (3H, s), 2.15 (3H, s), 5.07 (2H, s), 5.19 (2H, s), 7.19 (1H, dd, J=8 Hz, J=2 Hz), 7.39 (1H, d, J=2 Hz), 7.57 (1H, d, J=8 Hz) ppm

EXAMPLE 2

Synthesis of 2,4-bis(hydroxymethyl)bromobenzene

An about 93:7 mixture (36.7 g) of 2,4-bis(acetoxymethyl)-bromobenzene and 2,6-bis(acetoxymethyl)bromobenzene was dissolved in methanol (183 ml) and cooled to 10° C. To this solution was added dropwise 10% aqueous sodium hydroxide solution (133 g). The reaction mixture was stirred at room temperature for 1 hr, and the solvent (about 200 ml) was evanorated The residue was neutralized with dilute hydrochloric acid (about 200 ml). To the neutralized solution was added toluene (150 ml) and the mixture was stirred at 80–85° C. for 1 hr and cooled. The resulting crystals were collected by filtration and dried under reduced pressure to give an about 93:7 mixture (22.2 g, 83.7%) of 2,4-bis(hydroxymethyl)bromobenzene and 2,6-bis(hydroxymethyl)-bromobenzene as almost white crystals. 2,4-bis(Hydroxymethyl)-bromobenzene was isolated by preparative HPLC and used in the measurement.
mixture:
melting point 106–108° C.;
IR(KBr)ν=3307 (br), 1467 (s), 1413 (s), 1228 (s), 1158 (s), 1063 (s), 1002 (s), 824 (s), 741 (s), 641 (s) cm$^{-1}$
2,4-bis(Hydroxymethyl)bromobenzene:
$^1$H-NMR(DMSO-d$_6$, 400 MHz)δ=4.46 (2H, d, J=5 Hz), 4.49 (2H, d, J=5 Hz), 5.26 (1H, t, J=5 Hz), 5.41 (1H, t, J=5 Hz), 7.12 (1H, dd, J=8 Hz, J=2 Hz), 7.48 (1H, d, J=8 Hz), 7.50 (1H, d, J=2 Hz) ppm

EXAMPLE 3

Synthesis of 2,4-bis(1'-ethoxyethoxymethyl) bromobenzene

To a suspension obtained by dispersing an about 93:7 mixture (22.1 g) of 2,4-bis(hydroxymethyl)bromobenzene and 2,6-bis(hydroxymethyl)bromobenzene, and p-toluenesulfonic acid monohydrate (0.1 g) in toluene (220 ml) was added dropwise ethyl vinyl ether (18.4 g) at 24–32° C., and the mixture was stirred at room temperature for 2 hr. The reaction mixture was poured into 5% aqueous sodium carbonate solution (100 ml), and the organic layer was washed with 5% aqueous sodium carbonate solution (100 ml), and dried over potassium carbonate. The solvent was evaporated to give an about 93:7 mixture (35.7 g, 97.1%) of 2,4-bis(1'-ethoxyethoxymethyl)bromobenzene and 2,6-bis (1'-ethoxyethoxymethyl)bromobenzene as a yellow oil. 2,4-bis(1'-Ethoxyethoxymethyl)bromobenzene was isolated by preparative HPLC and used in the measurement.
2,4-bis(1'-Ethoxyethoxymethyl)bromobenzene:
$^1$H-NMR(CDCl$_3$, 400 MHz)δ=1.22 (3H, t, J=7 Hz), 1.23 (3H, t, J=7 Hz), 1.36 (3H, d, J=5 Hz), 1.41 (3H, d, J=5 Hz), 3.48–3.59 (2H, m), 3.63–3.75 (2H, m), 4.49 (1H, d, J=12 Hz), 4.58 (1H, d, J=13 Hz), 4.61 (1H, d, J=12 Hz), 4.69 (1H, d, J=13 Hz), 4.81 (1H, q, J=5 Hz), 4.88 (1H, q, J=5 Hz), 7.14 (1H, dd, J=8 Hz, J=2 Hz), 7.47 (1H, d, J=2 Hz), 7.50 (1H, d, J=8 Hz) ppm

EXAMPLE 4

Synthesis of 2,4-bis(methoxymethyl)bromobenzene

To a solution of m-xylylene dichloride (25.0 g) in methanol (125 ml) was added a 28% methanol solution (82.6 g) containing sodium methoxide at room temperature, and the mixture was stirred with heating at 60° C. for 3 hr. The solvent was evaporated and water (150 ml) was added to the residue. The mixture was extracted twice with heptane (80 ml) and heptane was evaporated under reduced pressure to give m-xylylene glycol dimethyl ether (25.3 g). m-Xylylene glycol dimethyl ether (25.3 g) was dissolved in acetic acid (125 ml) and sodium acetate (68 g) was added, which was followed by dropwise addition of bromine (68 g) at room temperature. The mixture was stirred at room temperature for 3 hr and poured into 10% aqueous sodium sulfite solution (750 ml), which mixture was extracted twice with heptane (350 ml). The heptane layer was extracted twice with 10% aqueous sodium hydroxide solution (150 ml) and once with water (150 ml). The solvent was evaporated and the residue was purified by silica gel column chromatography using heptane-ethyl acetate (15:1) as an eluent to give the title compound (10.4 g, yield: 29.7%) as a colorless transparent oil.

2,4-bis(Methoxymethyl)bromobenzene:

$^1$H-NMR(CDCl$_3$, 400 MHz)δ=3.38 (3H, s), 3.53 (3H, s), 4.42 (2H, s), 4.52 (2H, s), 7.13 (1H, dd, J=8 Hz, J=2 Hz), 7.43 (1H, d, J=2 Hz), 7.51 (1H, d, J=8 Hz) ppm

EXAMPLE 5

Synthesis of 1-(4'-fluorophenyl)-1,3-dihydroisobenzofuran-5-ylmethanol

An about 93:7 mixture (34.7 g) of 2,4-bis(1'-ethoxyethoxymethyl)bromobenzene and 2,6-bis(1'-ethoxyethoxymethyl)bromobenzene was dissolved in dehydrated tetrahydrofuran (250 ml) under a nitrogen atmosphere and cooled to −40° C. Thereto was added dropwise a hexane solution (1.57 mol/L, 64.3 ml) of n-butyllithium at a temperature of from −40° C. to −30° C. The mixture was heated to −20° C. and thereto was added dropwise p-fluorobenzaldehyde (12.5 g). The mixture was allowed to warm to 15° C. over 1 hr. The reaction mixture was poured into 20% aqueous ammonium chloride solution (200 ml) and the organic layer was separated. The aqueous layer was extracted with toluene (200 ml). The combined organic layer was washed twice with 20% brine (250 ml) and the solvent was evaporated. To the residue (38.5 g) was added 60% phosphoric acid (300 g) and the resulting solution was stirred at 80–85° C., 9.31–13.3 kPa. (70–100 Torr) for 2 hr with heating and cooled to 10° C. The resulting crystals were collected by filtration, washed thoroughly with ethanol and dried to give 1-(4'-fluorophenyl)-1,3-dihydroisobenzofuran-5-ylmethanol (20.8 g, 88.7%) as fine yellow crystals.

melting point 101–104° C.;

IR(KBr)ν=3214 (br), 2848 (w), 1606 (s), 1511 (s), 1225 (s), 1157 (m), 1135 (m), 1046 (s), 1015 (s), 824 (s), 810 (s), 783 (m) cm$^{-1}$;

$^1$H-NMR(CDCl$_3$, 400 MHz)δ=4.72 (2H, s), 5.19 (1H, d, J=12 Hz), 5.31 (1H, d, J=12 Hz), 6.14 (1H, s), 6.98 (1H, d, J=8 Hz), 7.03 (2H, t, J=9 Hz), 7.24 (1H, d, J=8 Hz), 7.29 (2H, dd, J=9 Hz, J=6 Hz), 7.32 (1H, s) ppm

EXAMPLE 6

Synthesis of 1-(4'-fluorophenyl)-1,3-dihydroisobenzofuran-5-carbaldehyde 1-(4'-Fluorophenyl)-1,3-dihydroisobenzofuran-5-ylmethanol (20.6 g) was dissolved in ethyl acetate (160 ml) and to the obtained solution were added sodium hydrogencarbonate (2.9 g), tetrabutylammonium bromide (1.6 g) and 4-hydroxy-2,2,6,6-tetramethyl-1-piperidinoxy (0.13 g). The mixture was cooled to 5° C. Thereto was added dropwise 12.9% aqueous sodium hypochlorite solution (52.7 g) at 5–10° C. and the mixture was stirred for 1 hr. Water (100 ml) was added to the reaction mixture and the mixture was extracted twice with ethyl acetate (100 ml). The extract was washed with 5% aqueous sodium hydrogencarbonate solution and saturated brine, and silica gel (3 g) was added. The mixture was filtered and the solvent was evaporated to give 1-(4'-fluorophenyl)-1,3-dihydroisobenzofuran-5-carbaldehyde (17.2 g, 84.2%).

$n_D^{24}$ 1.5823;

IR(neat)ν=3071 (w), 2857 (m), 2743 (w), 1697 (s), 1605 (s), 1509 (s), 1225 (s), 1157 (m), 1144 (m), 1045 (s), 832 (s), 816 (s), 786 (m) cm$^{-1}$;

$^1$H-NMR(CDCl$_3$, 400 MHz)δ=5.25 (1H, d, J=13 Hz), 5.38 (1H, d, J=13 Hz), 6.18 (1H, s), 7.06 (2H, t, J=9 Hz), 7.16 (1H, d, J=8 Hz), 7.30 (2H, d, J=9 Hz, J=5 Hz), 7.77 (1H, d, J=8 Hz), 7.83 (1H, s), 10.03 (1H, s) ppm

EXAMPLE 7

Synthesis of 1-(4'-fluorophenyl)-1,3-dihydroisobenzofuran-5-carbaldehyde oxime 1-(4'-Fluorophenyl)-1,3-dihydroisobenzofuran-5-carbaldehyde (5.96 g) was dissolved in toluene (30 ml) and triethylamine (2.75 g) was flown in. Thereto was added hydroxylamine hydrochloride (1.88 g) and the mixture was reacted at 80–90° C. for 1 hr. Hot water (30 ml) was added to the reaction mixture and the mixture was partitioned while hot at 90° C. The organic layer was cooled to 0–5° C. and the resulting crystals were collected by filtration to give the title compound (5.02 g, yield: 79.2%).

melting point 158–159° C.;

$^1$H-NMR(CDCl$_3$, 400 MHz)δ=5.19 (1H, d, J=13 Hz), 5.32 (1H, d, J=13 Hz), 6.14 (1H, s), 7.01 (1H, d, J=8 Hz), 7.04 (2H, t, J=9 Hz), 7.29 (2H, dd, J=9 Hz, J=5 Hz), 7.43 (1H, d, J=8 Hz), 7.53 (1H, s), 7.82 (1H, br), 8.16 (1H, s) ppm

EXAMPLE 8

Synthesis of 1-(4'-fluorophenyl)-1,3-dihydroisobenzofuran-5-carbonitrile 1-(4'-Fluorophenyl)-1,3-dihydroisobenzofuran-5-carbaldehyde (17.00 g) was dissolved in toluene (200 ml) and hydroxylamine hydrochloride (5.5 g) and triethylamine (8.0 g) were added. The mixture was stirred at 80–100° C. for 2 hr. The obtained triethylamine hydrochloride was filtered and the solvent was evaporated. Thereto was added acetic anhydride (36.5 g) and the mixture was stirred at 125–130° C. for 5 hr. The reaction mixture was poured into 10% aqueous sodium hydroxide solution (300 ml) and extracted twice with toluene (200 ml). The toluene layer was washed successively with 5% aqueous sodium hydroxide solution, water and saturated brine and dried over magnesium sulfate. Silica gel (5 g) was added and the mixture was thoroughly stirred and filtered. The solvent was evaporated to give crude 1-(4'-fluorophenyl)-1,3-dihydroisobenzofuran-5-carbonitrile (14.2 g). This was recrystallized from a mixed solvent of ethanol/hexane to give 1-(4'-fluorophenyl)-1,3-dihydroisobenzofuran-5-carbonitrile (9.52 g, 59.8%).

melting point 96–98° C.;

IR(KBr)ν=3050 (w), 2867 (m), 2228 (s), 1603 (s), 1510 (s), 1224 (s), 1157 (m), 1048 (s), 1031 (s), 832 (s) cm$^{-1}$;

$^1$H-NMR(CDCl$_3$, 400 MHz)δ=5.21 (1H, d, J=13 Hz), 5.34 (1H, d, J=13 Hz), 6.16 (1H, s), 7.06 (2H, t, J=9 Hz), 7.10 (1H, d, J=8 Hz), 7.27 (2H, dd, J=9 Hz, J=5 Hz), 7.55 (1H, d, J=8 Hz), 7.60 (1H, s) ppm

REFERENCE EXAMPLE 1

Synthesis of m-xylylene glycol diacetate m-Xylylene dichloride (25.0 g, 143 mmol) and potassium acetate (34.0 g, 171 mmol) were suspended in acetone (125 ml). To the suspension was added benzyltriethylammonium chloride (4.8 g) and the mixture was refluxed for 2.5 hr. The reaction mixture was cooled and filtered. The solvent was evaporated and toluene (50 ml) was added. The toluene layer was washed with water (50 ml) and saturated brine (50 ml) and the solvent was evaporated to give m-xylene glycol diacetate (31.3 g, 98.7%) as an oil.

REFERENCE EXAMPLE 2

Synthesis of 1-(3'-dimethylaminopropyl)-1-(4'-fluorophenyl)-1,3-dihydroisobenzofuran-5-carbonitrile (citalopram)

60% Sodium hydride (0.92 g) was dispersed in THF (30 ml). To the obtained suspension was added dropwise a solution of 1-(4'-fluorophenyl)-1,3-dihydroisobenzofuran-5-carbonitrile (4.80 g) in THF (10 ml) at 40–50° C. The mixture was stirred at the same temperature for 30 min, and a solution of 3-dimethylaminopropyl chloride (3.2 g) in toluene (20 ml) was added dropwise, which was followed by stirring for 10 min. Then, dimethyl sulfoxide (30 ml) was further added dropwise and the mixture was stirred at 65–70° C. for 3 hr. The reaction mixture was poured into ice water (200 ml) and extracted 3 times with toluene (60 ml). The organic layer was extracted twice with 20% aqueous acetic acid (60 ml). The aqueous layer was neutralized, extracted twice with toluene (60 ml) and washed with water. Anhydrous potassium carbonate (2 g) and silica gel (2 g) were added and the mixture was stirred and filtered. The solvent was evaporated to give 1-(3'-dimethylaminopropyl)-1-(4'-fluorophenyl)-1,3-dihydroisobenzofuran-5-carbonitrile (citalopram base) as a viscous oil (3.37 g, 51.6%).

This oil was converted to hydrobromide by a conventional method. The melting point of the obtained crystals was 184–186° C.

$^1$H-NMR(CDCl$_3$, 400 MHz)δ=1.26–1.52 (2H, m), 2.11–2.26 (4H, m), 2.13 (6H, s), 5.15 (1H, d, J=13 Hz), 5.19 (1H, d, J=13 Hz), 7.00 (2H, t, J=9 Hz), 7.41 (1H, d, J=8 Hz), 7.43 (2H, dd, J=9 Hz, J=5 Hz), 7.50 (1H, s), 7.59 (1H, d, J=8 Hz) ppm According to the present invention, an industrially advantageous production method capable of producing a 5-phthalancarbonitrile compound at a high yield can be provided without using a reagent that imposes a great burden on the environment (with small environmental burden), such as heavy metal, metal cyanide and thionyl chloride. From the obtained 5-phthalancarbonitrile compound, citalopram useful as an antidepressant can be provided.

This application is based on a patent application No. 311703/1999 filed in Japan, the contents of which are hereby incorporated by reference.

What is claimed is:
1. A production method of a compound of the formula [I]

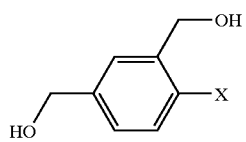

[I]

wherein X is chlorine atom, bromine atom or iodine atom, which comprises subjecting a compound of the formula [A]

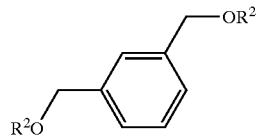

[A]

wherein R$^2$ is alkanoyl having 2 to 5 carbon atoms, to chlorination, bromination, or iodination and then to elimination of the alkanoyl group.

2. The method of claim 1, further comprising reacting the compound of formula [I] with a reagent to form a compound of formula [II-b]

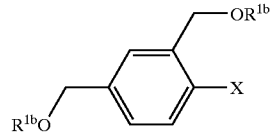

[II-b]

wherein R$^{1b}$ is an alkyl having 1 to 5 carbon atoms, tetrahydropyran-2-yl, alkoxymethyl wherein the alkoxyl moiety has 1 to 5 carbon atoms, 1-alkoxyethyl wherein the alkoxyl moiety has 1 to 10 carbon atoms, or trialkylsilyl wherein each alkyl moiety has 1 to 5 carbon atoms, and X is a chlorine atom, bromine atom, or iodine atom, and coupling the compound of formula [II-b] with p-fluorobenzaldehyde to form the a compound of formula [III]

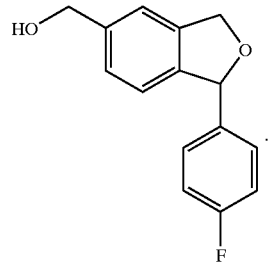

[III]

3. The method of claim 2, further comprising oxidizing the compound of formula [III] to form a compound of formula [IV]

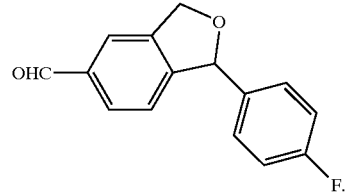

[IV]

4. The method of claim 3, further comprising combining the compound of formula [IV] with hydroxylamine or a mineral acid salt thereof to form a compound of formula [V]

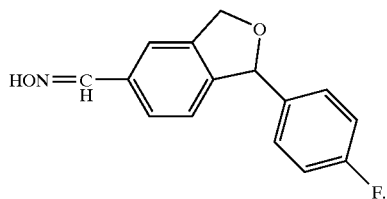

[V]

5. The method of claim 4, further comprising dehydrating the compound of formula [V] into a compound of formula [VI]

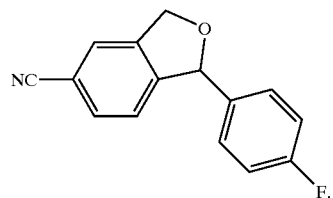

[VI]

6. The method of claim 5, further comprising the step of alkylating the compound of formula [VI] with dimethylaminopropyl halide to form citalopram, and optionally isolating citalopram or a hydrobromide salt thereof.

* * * * *

UNITED STATES PATENT AND TRADEMARK OFFICE
CERTIFICATE OF CORRECTION

PATENT NO. : 6,930,211 B2
DATED : August 16, 2005
INVENTOR(S) : Ikemoto et al.

It is certified that error appears in the above-identified patent and that said Letters Patent is hereby corrected as shown below:

Column 20,
Line 38, "form the a compound" should read -- form a compound --.

Signed and Sealed this

Twenty-seventh Day of December, 2005

JON W. DUDAS
*Director of the United States Patent and Trademark Office*